(12) United States Patent
Sohn

(10) Patent No.: US 9,622,624 B2
(45) Date of Patent: Apr. 18, 2017

(54) ENDOTHERMIC TOWEL

(71) Applicant: Dae Up Sohn, Seoul (KR)

(72) Inventor: Dae Up Sohn, Seoul (KR)

(*) Notice: Subject to any disclaimer, the term of this patent is extended or adjusted under 35 U.S.C. 154(b) by 166 days.

(21) Appl. No.: 14/391,675

(22) PCT Filed: Mar. 28, 2014

(86) PCT No.: PCT/KR2014/002636
§ 371 (c)(1),
(2) Date: Oct. 9, 2014

(87) PCT Pub. No.: WO2014/157972
PCT Pub. Date: Oct. 2, 2014

(65) Prior Publication Data
US 2015/0075187 A1 Mar. 19, 2015

(30) Foreign Application Priority Data
Mar. 29, 2013 (KR) .................. 10-2013-0034483

(51) Int. Cl.
*A47K 10/02* (2006.01)
*A61F 7/10* (2006.01)
*F25D 5/02* (2006.01)

(52) U.S. Cl.
CPC ............ *A47K 10/02* (2013.01); *A61F 7/10* (2013.01); *F25D 5/02* (2013.01)

(58) Field of Classification Search
CPC ... A47K 10/02; A61F 7/02; A61F 7/10; F25D 5/02
USPC ....................................... 428/102
See application file for complete search history.

(56) References Cited

U.S. PATENT DOCUMENTS 8,440,119 B2 5/2013 Ackroyd et al.
2007/0256261 A1* 11/2007 Benitez et al. ............ 15/118

FOREIGN PATENT DOCUMENTS

| JP | 1997-170108 A | 6/1997 |
|---|---|---|
| JP | 2000-083986 A | 3/2000 |
| JP | 2000-095679 A | 4/2000 |
| JP | 2001-198151 A | 7/2001 |
| JP | 2004-141575 A | 5/2004 |
| JP | 2004-215693 A | 8/2004 |
| JP | 2005-187994 A | 7/2005 |
| JP | 2010-057872 A | 3/2010 |
| KR | 20-1991-0006107 Y1 | 8/1991 |
| KR | 10-2006-0059854 A | 6/2006 |
| KR | 10-2012-0133048 A | 12/2012 |
| WO | 2005/068916 A1 | 7/2005 |

* cited by examiner

*Primary Examiner* — Brent O'Hern
(74) *Attorney, Agent, or Firm* — Novick, Kim & Lee, PLLC; Jae Youn Kim

(57) ABSTRACT

Disclosed is an endothermic towel which causes an endothermic reaction with moisture of a human body to remove a thermal feeling and to simultaneously dry moisture in a short time. The towel includes: a first towel member having an exothermic function; and a second towel member having a ventilating function, wherein the first and second towel members are integrated with each other by sewing edges of the first and second towel members, so that the skin temperature may be effectively dropped down, a feeling of use may be improved and the low-temperature state may be more efficiently maintained.

6 Claims, 5 Drawing Sheets

ENDOTHERMIC TOWEL

TECHNICAL FIELD

The present invention relates to an endothermic towel, and more particularly, to an endothermic towel which causes an endothermic reaction with moisture of a human body to remove a thermal feeling and to simultaneously dry moisture in a short time.

BACKGROUND ART

Conventionally, there has been used a method of providing a cool feeling by wearing a towel or facecloth, which is wet in water, around a user neck in order to give a cool feeling while the user is exposed to sunlight in viewing outdoor sports or at an outdoor working place.

However, according to such a method, when a wet towel or facecloth is used, the user is made to feel uncomfortable due to residual moisture on his skin and his clothes are wet.

In addition, although a small amount of a component, such as menthol, sorbitol, or peppermint oil, is contained in pain relieving patch or cosmetics used as quasi-drugs in order to give a feeling of refreshment to the skin of a user, the component does not really allow the skin temperature of a user to fall and, when a large amount of the component is used, it has been known that the component seriously stimulates the skin, specifically, so that it has many restrictions to be used for a face.

In addition, as anther method of providing a cool feeling, it has been known to use a lotion melt when the lotion makes contact with a user. The melting heat taken from a user is used to melt the lotion. Since heat is taken from a user without changing the temperature concerned with the melting procedure, the skin is really cooled. That is, materials for providing a cool feeling to a user have been developed by using a heat absorbing material.

As well as the above described materials, recently, by using a fabric of a PVC material having an excellent absorptiveness, a towel (which is called 'a cool towel'), which lowers the body temperature of a part making contact with the body of a user and circulates the increased moisture to an outside of the fabric, has been developed and sold.

For example, as shown in FIG. 1, a towel, which uses a fabric having a honeycomb structure, which absorbs moisture about 1.5 times greater than the amount of moisture absorbed by a general fabric to give a cool feeling to a user, has been sold.

Meanwhile, examples of a technique of giving a cool feeling to a user by using an endothermic reaction have been disclosed in the following documents.

For example, a hempen hood, in which an absorptive material such as absorptive polymer is embedded to maintain a cool feeling at a worn portion due to heat of vaporization when a supporter viewing sports in mid-summer wears it on an occipital region, has been disclosed in Japanese Unexamined Patent Publication No. 1997-170108 (Jun. 30, 1997).

Further, spice including menthol and peppermint, cooling agent, or cooling solution obtained by diluting alcohol, which is impregnated into a main receiving part of clothes to maintain a feeling of refreshment for a long time when a work or sports are done at an outdoor place, has been disclosed in Japanese Unexamined Patent Publication No. 2000-095679 (Apr. 4, 2000).

In addition, an absorptive fiber sheet containing at least one kind of chemicals causing exothermic or endothermic reaction when the chemicals are non-thermally stimulated in an outside application has been disclosed in PCT Publication No. WO2005/068916 (Jul. 28, 2005).

DISCLOSURE

Technical Problem

However, since chemicals or absorbers are used in techniques disclosed in the patent documents described above, the use of the chemicals or absorbers is complex. In addition, the chemicals or absorbers are harmful to health if the chemicals or absorbers are repeatedly used or are exposed to a human body.

In addition, when the towel shown in FIG. 1 is used, an exothermic amount of the towel is reduced or the towel itself droops or causes a bad smell due to repeated use. That is, when the towel shown in FIG. 1 is repeatedly used through washings of the towel, the flexibility of the towel is entirely deteriorated so that the absorbing function of the towel is deteriorated, so it is impossible to repeatedly use the towel.

When the towel shown in FIG. 1 is used between the skin and the clothes of a user, for example, between the neck and the shirt of a user, the towel is pressed by the shirt, so that the exothermic function of the towel is deteriorated and the shirt is wet.

Further, in the structure shown in FIG. 1, it is inconvenient that a user visually recognizes and distinguishes the front and rear surfaces of the towel according to the exothermic and endothermic functions of the towel and distinguishes the front and rear surfaces of the towel from each other to use the towel.

To solve the above problems, an object of the present invention is to provide an endothermic towel which can maintain the flexibility of a towel even through the towel is washed to be repeatedly used.

It is another object of the present invention to provide an endothermic towel which can maintain the exothermic property of a towel by manufacturing the towel in a dual structure without regard to a using condition.

It is still another object of the present invention to provide an endothermic towel which can allow a user to visually distinguish the front and rear surfaces thereof from each other such that the endothermic towel is easily used.

It is still another object of the present invention to provide an endothermic towel which can deteriorate a bad smell caused due to the repeated use.

Technical Solution

To achieve the above objects, according to present invention, there is provided a towel which causes an endothermic reaction with moisture of a human body to remove a thermal feeling. The towel includes: a first towel member having an exothermic function; and a second towel member having a ventilating function, wherein the first and second towel members are integrated with each other by sewing edges of the first and second towel members together.

In the towel according to the present invention, the first and second towel members have mutually different colors.

In the towel according to the present invention, contact surfaces of the first and second towel members are spaced apart from each other to define a space part.

In the towel according to the present invention, the first towel member is formed of a fiber having high absorptiveness and flexibility, and the second towel member has a mesh shape.

In the towel according to the present invention, the first or second towel member contains a xylitol component having an endothermic function.

In the towel according to the present invention, the sewing is executed by using a flexible sewing thread.

In the towel according to the present invention, the first or second towel member contains a coffee component having a deodorizing function.

In the towel according to the present invention, moisture of the first towel member is discharged through the mesh of the second towel member to an outside.

In the towel according to the present invention, the second towel member is formed of an inflexible fiber.

In the towel according to the present invention, contact surfaces of the first and second towel members are partially sewed.

Advantageous Effects

As described above, according to the towel of the present invention, there are provided the first towel member having an exothermic function and the second towel member having a ventilating function, so that the exothermic function may be maintained without regard to a using situation of a user and the temperature may be effectively dropped down while a skin state is maintained to be dried out. Thus, a feeling of use may be improved and a low-temperature state may be more efficiently maintained. In addition, since the contact surfaces of the first and second towel members are spaced apart from each other so that the space part is formed and the second mesh member has the mesh shape, the exothermic property may be improved.

According to the towel of the present invention, since the second towel member is formed of an inflexible fiber, the flexibility of the first towel member may be maintained even though the towel is repeatedly used through washing thereof. That is, any washing dedicated nets for preventing a towel from drooping as in a towel of the related art are not required to wash the towel.

According to the towel of the present invention, since the first and second towel members contain a xylitol component having an endothermic function, the exothermic property of the towel may be more improved.

According to the towel of the present invention, the first and second towel members are sewed by using the flexible sewing thread, the flexibility of the first towel member may be maintained.

According to the towel of the present invention, since the first and second towel members have mutually different colors, a user may distinguish visually and easily the front and rear surfaces of the towel from each other so that the towel is effectively used.

In addition, according to the towel of the present invention, since the first or second towel member has a deodorizing function, any bad smell of the towel may be reduced even though the towel is repeatedly used.

BEST MODE

[Mode for Invention]

The above objects, another object, and new features of the present invention will be more apparent from the description and accompanying drawings of this specification.

Hereinafter, a configuration of an endothermic towel according to an embodiment of the present invention will be described with reference to FIGS. 2 and 3.

Figure 2:
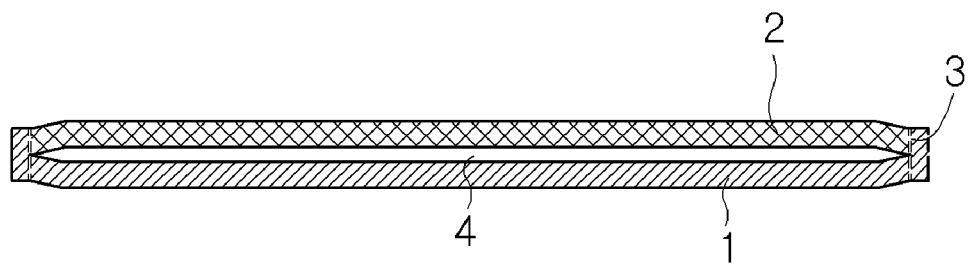
FIG. 2 is a sectional view showing an endothermic towel according to an embodiment of the present invention.

FIG. 2 is a sectional view showing an endothermic towel according to an embodiment of the present invention. FIG. 3 is a perspective view of the endothermic towel shown in FIG. 2.

Figure 1:
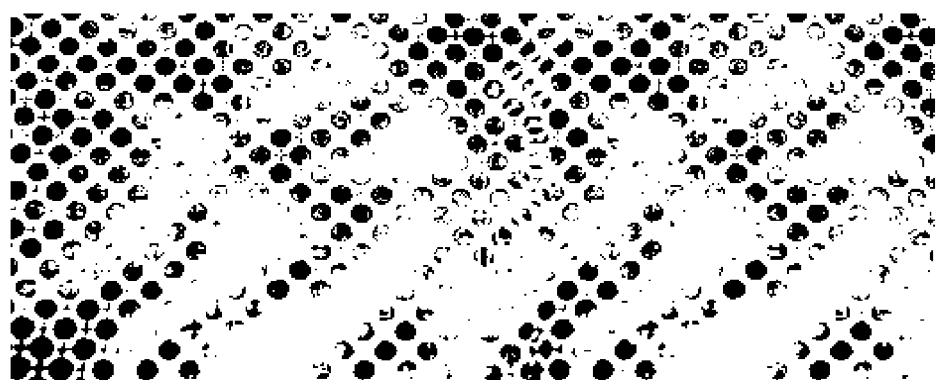
FIG. 1 is a photograph showing one example of a structure of a towel according to the related art.

As shown in FIGS. 1 and 2, a towel according to the present invention, which causes an endothermic reaction with moisture of a human body to remove a thermal feeling, includes a first towel member 1 having an exothermic function, and a second towel member provided on the first towel member 1 to have a ventilating function. The first and second towel members 1 and 2 are integrated with each other by sewing edges of the first and second towel members 1 and 2.

As described above, since the sewing between the first and second towel members 1 and 2 is executed by using a sewing thread 3 at the edges of the first and second towel members 1 and 2, as shown in FIG. 1, the contact surfaces of the first and second towel members 1 and 2 are spaced apart from each other such that a space part 4 is formed.

Although the towel according to the present invention has a substantially rectangular shape like a conventional towel, the present invention is not limited thereto. The towel can be prepared even in a square shape like a handkerchief or in a triangular shape according to a purpose of use. In addition, a size of the towel may be increased or decreased according to purpose of use, and the present invention may not limit the size of the towel.

Meanwhile, the first towel member 1 is formed of a flexible fiber. As shown in FIG. 2, the second towel member 2 has a mesh shape. That is, the first towel member 1 is formed of a high-absorbable and flexible fiber, and the second towel member 2 is formed of an inflexible fiber. In addition, a size of a mesh formed in the second towel member 2 is not limited to any specific sizes. Thus, it is sufficient if the mesh has a size enough to enable an inside of the first towel member 1 to communicate with an outside of the second towel member 2 to perform an endothermic process in the first towel member 1.

Thus, the moisture absorbed into the first towel member 1 is vaporized through the mesh provided in the second towel member 2. That is, since the space part is formed between the first and second towel members 1 and 2 and the second towel member 2 is formed in a mesh shape, the exothermic property may be more improved. In addition, since the second towel member 2 has no moisture, when the towel is used between the neck and shirt of a user, the problem that the towel is pressed by the shirt, so that the exothermic function of the towel is deteriorated and the shirt is wet may be solved.

Figure 3:
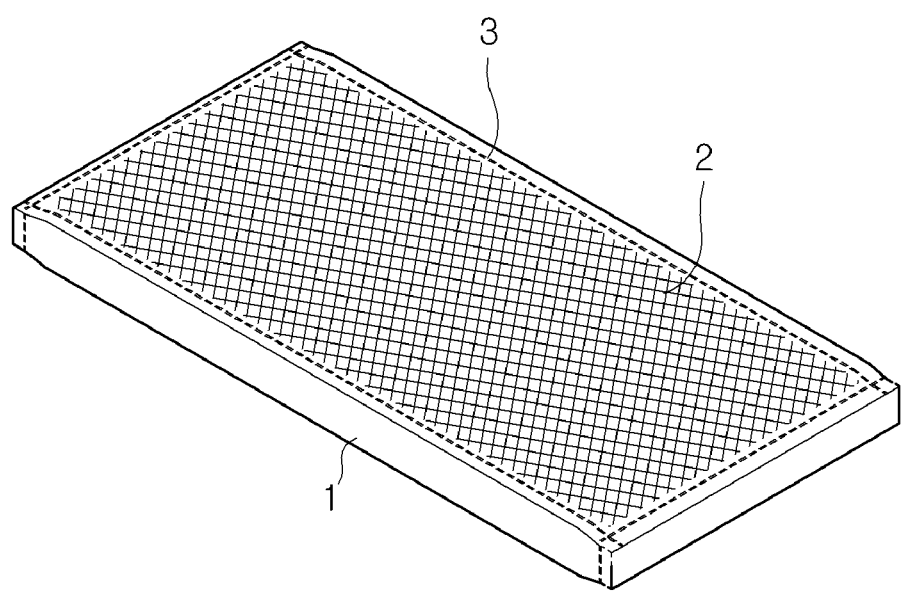
FIG. 3 is a perspective view of the endothermic towel shown in FIG. 2.

In addition, the sewing is performed by using the flexible sewing thread 3, and, as shown in FIGS. 2 and 3, a part of the first towel member 1 overlaps the second towel member 2. That is, the first towel member 1 is sewed while surrounding the second towel member 2 having the mesh structure, so that an edge of the second towel member 2 may be prevented from being damaged.

In addition, although the structure, in which the first and second towel members 1 and 2 are integrated with each other through the sewing, has bee described in the embodiment, the present invention is not limited thereto, but a structure may be employed, in which the second towel member 2 adheres to the first towel member 1.

In addition, when the sewing thread 3 formed of the same flexible material as that of the first towel member 1 is used, the second towel member 2 may be prevented from being damaged due to the flexibility of the first towel member 1.

A fabric product containing a component of xylitol, erythritol or a mixture of them which provides endothermic effect and a feeling of refreshment for each of the first and second towel members 1 and 2 may be used. Thus, since the towel according to the present invention contains the xylitol component, the exothermic property of the towel may be improved.

A fabric product containing a coffee component having a deodorizing function for the first or second towel member 1 or 2 may be used. Thus, since the first or second towel member 1 or 2 has a deodorizing function, any bad smell of the towel may be reduced even though the towel is repeatedly used.

Hereinafter, another embodiment of the present invention will be described with reference to FIG. 4.

Figure 4:
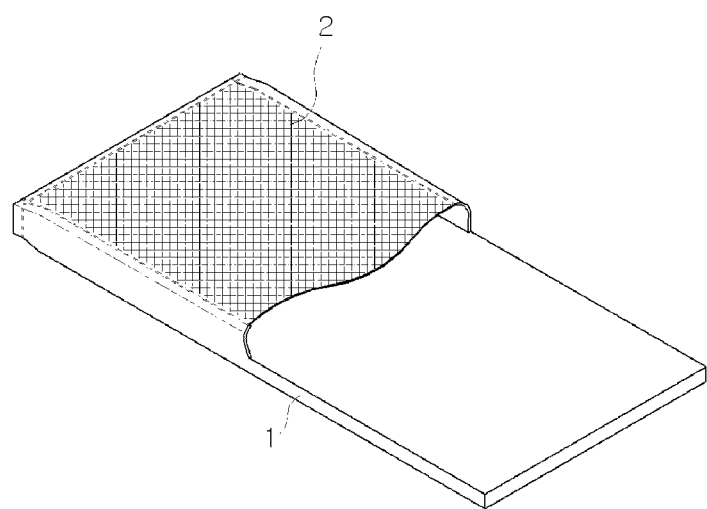
FIG. 4 is a perspective view showing an endothermic towel according to another embodiment of the present invention.

FIG. 4 is a perspective view showing an endothermic towel according to another embodiment of the present invention. In FIG. 4, the second towel member 2 is partially cut to illustrate a difference between the colors of the first and second towel members 1 and 2.

As shown in FIG. 4, the towel according to another embodiment of the present invention includes the first and second towel members 1 and 2 having mutually different colors. Since the elements of the towel according to another embodiment is equal to those of the towel according to the above described embodiment except for the colors of the first and second towel members 1 and 2, the details will be omitted As shown in FIG. 4, although the first and second towel members 1 and 2 having green and blue colors, respectively has been described in another embodiment of the present invention, the present invention is not limited thereto and the first and second towel members 1 and 2 may have various colors to the extent that they can be distinguished from each other.

As described above, since the first and second towel members 1 and 2 have mutually different colors, the user may visually distinguish the first towel member 1, which may be wet, from the second towel member 2. That is, the user may distinguish visually and easily the front and rear surfaces of the towel from each other, so that the user effectively uses the towel.

Hereinafter, still another embodiment of the present invention will be described with reference to FIG. 5.

Figure 5:
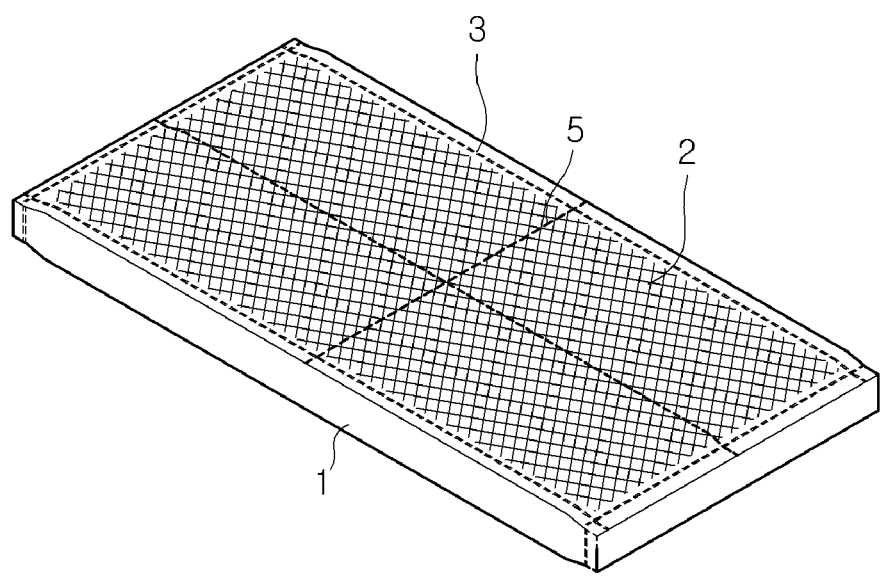
FIG. 5 is a perspective view showing an endothermic towel according to still another embodiment of the present invention.

FIG. 5 is a perspective view showing an endothermic towel according to still another embodiment of the present invention.

When a towel applied to the present invention has a very long length, the first towel member 1 may sag (droop) downwardly.

To solve the above problem, according to still another embodiment of the present invention, as shown in FIG. 5, central portions of the first and second towel members 1 and 2 are cross-sewed to cross each other. In addition, a cross-sewing thread 5 applied to the embodiment is formed of a flexible material like the sewing thread 3, so that the second towel member 2 may be prevented from being damaged due to the flexibility of the first towel member 1.

Meanwhile, although only one cross-sewing is depicted in FIG. 5 for the purpose of convenience of description, the embodiment is not limited thereto and a plurality of cross-sewing executions may be performed according to a size of the towel or along one side of the towel.

That is, according to the present invention, in order to prevent the first towel member formed of a fiber having high absorptiveness and flexibility from drooping while the contact surfaces of the first and second towel members are maintained to be spaced apart to from each other according to the size of the towel to form a space part if possible, parts of the contact surfaces of the first and second towel members 1 and 2 may be sewed.

Although an exemplary embodiment of the present invention has been described for illustrative purposes, those skilled in the art will appreciate that various modifications, additions and substitutions are possible, without departing from the scope and spirit of the invention as disclosed in the accompanying claims.

INDUSTRIAL APPLICABILITY

When the endothermic towel according to the present invention is used, the skin temperature of a user may effectively fall, a feeling of use may be improved, and a low-temperature state may be more effectively maintained.

The invention claimed is:

1. A towel, which causes an endothermic reaction with moisture of a human body to remove a thermal feeling, the towel comprising:
   a first towel member for absorbing moisture; and
   a second towel member having a mesh shape and vaporizing the moisture absorbed in the first towel member by ventilation,
   wherein the first and second towel members are integrated with each other by sewing edges of the first and second towel members together,
   wherein contact surfaces of the first and second towel members are capable of being spaced apart from each other to define a space part,
   wherein the mesh of the second towel member is configured to discharge the moisture of the first towel member to an outside,
   wherein the first towel member is formed of a fiber having a higher absorptiveness and flexibility than those of the second towel member, and
   wherein the second towel member is less flexible than that of the first towel member.

2. The towel of claim 1, wherein the first and second towel members have mutually different colors.

3. The towel of claim 1, wherein the first or second towel member contains a xylitol component having an endothermic function.

4. The towel of claim 1, wherein the sewing is executed by using a sewing thread having a flexibility same as that of the first towel member.

5. The towel of claim 1, wherein the first or second towel member contains a coffee component having a deodorizing function.

6. The towel of claim 1, wherein the contact surfaces of the first and second towel members are partially sewed.

\* \* \* \* \*